United States Patent
Folkerts et al.

(10) Patent No.: US 11,541,252 B2
(45) Date of Patent: Jan. 3, 2023

(54) DEFINING DOSE RATE FOR PENCIL BEAM SCANNING

(71) Applicant: Varian Medical Systems, Inc., Palo Alto, CA (US)

(72) Inventors: Michael Folkerts, Carrollton, TX (US); Eric Abel, San Jose, CA (US); Simon Busold, Cologne (DE); Jessica Perez, Geneva (CH); Vidhya Krishnamurthi, Los Altos, CA (US); C. Clifton Ling, Palo Alto, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 194 days.

(21) Appl. No.: 16/909,834

(22) Filed: Jun. 23, 2020

(65) Prior Publication Data
US 2021/0393981 A1 Dec. 23, 2021

(51) Int. Cl.
*A61N 5/10* (2006.01)
*G16H 20/40* (2018.01)
*A61B 6/00* (2006.01)

(52) U.S. Cl.
CPC .......... *A61N 5/1031* (2013.01); *A61B 6/4071* (2013.01); *A61N 5/10* (2013.01); *A61N 5/1042* (2013.01); *A61N 5/1077* (2013.01); *G16H 20/40* (2018.01); *A61N 2005/1087* (2013.01)

(58) Field of Classification Search
CPC ........ A61N 5/10; A61N 5/103; A61N 5/1031; A61N 5/1042; A61N 5/1043; A61N 5/1077; A61N 5/1078; A61N 2005/1085; A61N 2005/1087

USPC .................................................... 378/64, 65
See application file for complete search history.

(56) References Cited

U.S. PATENT DOCUMENTS

| | | |
|---|---|---|
| 4,163,901 A | 8/1979 | Azam |
| 4,914,681 A | 4/1990 | Klingenbeck et al. |
| 5,153,900 A | 10/1992 | Nomikos et al. |
| 5,267,294 A | 11/1993 | Kuroda |
| 5,550,378 A | 8/1996 | Skillicorn et al. |
| 5,610,967 A | 3/1997 | Moorman et al. |
| 5,625,663 A | 4/1997 | Swerdloff et al. |
| 5,682,412 A | 10/1997 | Skillicorn et al. |
| 5,757,885 A | 5/1998 | Yao et al. |
| 6,198,802 B1 | 3/2001 | Elliott et al. |

(Continued)

FOREIGN PATENT DOCUMENTS

| | | |
|---|---|---|
| CN | 104001270 | 8/2014 |
| CN | 106730407 | 5/2017 |

(Continued)

OTHER PUBLICATIONS

P. Lansonneur et al., First proton minibeam radiation therapy treatment plan evaluation, Scientific Reports, 10: 7025 (2020). (Year: 2020).*

(Continued)

*Primary Examiner* — Allen C. Ho

(57) ABSTRACT

The dose rate of voxels within a particle beam (e.g., proton beam) treatment field delivered using pencil beam scanning (PBS) is calculated, and a representative dose rate for the particle beam treatment field is reported. The calculations account for a dose accumulation in a local region or a sub-volume (e.g., a voxel) as a function of time.

21 Claims, 5 Drawing Sheets
(4 of 5 Drawing Sheet(s) Filed in Color)

(56) References Cited

U.S. PATENT DOCUMENTS

| | | | |
|---|---|---|---|
| 6,222,544 B1 | 4/2001 | Tarr et al. | |
| 6,234,671 B1 | 5/2001 | Solomon et al. | |
| 6,260,005 B1 | 7/2001 | Yang et al. | |
| 6,379,380 B1 | 4/2002 | Satz | |
| 6,411,675 B1 | 6/2002 | Llacer | |
| 6,445,766 B1 | 9/2002 | Whitham | |
| 6,504,899 B2 | 1/2003 | Pugachev et al. | |
| 6,580,940 B2 | 6/2003 | Gutman | |
| 6,993,112 B2 | 1/2006 | Hesse | |
| 7,268,358 B2 | 9/2007 | Ma et al. | |
| 7,453,983 B2 | 11/2008 | Schildkraut et al. | |
| 7,515,681 B2 | 4/2009 | Ebstein | |
| 7,522,706 B2 | 4/2009 | Lu et al. | |
| 7,560,715 B2 | 7/2009 | Pedroni | |
| 7,590,219 B2 | 9/2009 | Maurer, Jr. et al. | |
| 7,616,735 B2 | 11/2009 | Maciunas et al. | |
| 7,623,623 B2 | 11/2009 | Raanes et al. | |
| 7,778,691 B2 | 8/2010 | Zhang et al. | |
| 7,807,982 B2 | 10/2010 | Nishiuchi et al. | |
| 7,831,289 B2 | 11/2010 | Riker et al. | |
| 7,835,492 B1 | 11/2010 | Sahadevan | |
| 7,839,973 B2 * | 11/2010 | Nord | A61N 5/103 378/65 |
| 7,907,699 B2 | 3/2011 | Long et al. | |
| 8,009,804 B2 * | 8/2011 | Siljamaki | A61N 5/1031 378/65 |
| 8,284,898 B2 | 10/2012 | Ho et al. | |
| 8,306,184 B2 | 11/2012 | Chang et al. | |
| 8,363,784 B2 * | 1/2013 | Sobering | G16H 20/40 378/65 |
| 8,401,148 B2 | 3/2013 | Lu et al. | |
| 8,406,844 B2 | 3/2013 | Ruchala et al. | |
| 8,559,596 B2 | 10/2013 | Thomson et al. | |
| 8,594,800 B2 * | 11/2013 | Butson | G16H 20/40 600/407 |
| 8,600,003 B2 | 12/2013 | Zhou et al. | |
| 8,613,694 B2 | 12/2013 | Walsh | |
| 8,636,636 B2 | 1/2014 | Shukla et al. | |
| 8,644,571 B1 | 2/2014 | Schulte et al. | |
| 8,693,629 B2 * | 4/2014 | Sgouros | A61N 5/103 378/65 |
| 8,716,663 B2 | 5/2014 | Brusasco et al. | |
| 8,836,332 B2 | 9/2014 | Shvartsman et al. | |
| 8,847,179 B2 | 9/2014 | Fujitaka et al. | |
| 8,903,471 B2 | 12/2014 | Heid | |
| 8,917,813 B2 | 12/2014 | Maurer, Jr. | |
| 8,948,341 B2 | 2/2015 | Beckman | |
| 8,958,864 B2 | 2/2015 | Amies et al. | |
| 8,983,573 B2 | 3/2015 | Carlone et al. | |
| 8,986,186 B2 | 3/2015 | Zhang et al. | |
| 8,992,404 B2 | 3/2015 | Graf et al. | |
| 8,995,608 B2 | 3/2015 | Zhou et al. | |
| 9,018,593 B2 * | 4/2015 | Luechtenborg | A61N 5/1043 250/389 |
| 9,018,603 B2 | 4/2015 | Loo et al. | |
| 9,033,859 B2 | 5/2015 | Fieres et al. | |
| 9,079,027 B2 | 7/2015 | Agano et al. | |
| 9,149,656 B2 | 10/2015 | Tanabe | |
| 9,155,908 B2 | 10/2015 | Meltsner et al. | |
| 9,192,786 B2 * | 11/2015 | Yan | A61N 5/1049 |
| 9,233,260 B2 | 1/2016 | Slatkin et al. | |
| 9,251,302 B2 * | 2/2016 | Brand | G06F 30/20 |
| 9,258,876 B2 | 2/2016 | Cheung et al. | |
| 9,283,406 B2 | 3/2016 | Prieels | |
| 9,308,391 B2 | 4/2016 | Liu et al. | |
| 9,330,879 B2 | 5/2016 | Lewellen et al. | |
| 9,333,374 B2 | 5/2016 | Iwata | |
| 9,468,777 B2 | 10/2016 | Fallone et al. | |
| 9,517,358 B2 | 12/2016 | Velthuis et al. | |
| 9,526,918 B2 | 12/2016 | Kruip | |
| 9,545,444 B2 | 1/2017 | Strober et al. | |
| 9,583,302 B2 | 2/2017 | Figueroa Saavedra et al. | |
| 9,636,381 B2 | 5/2017 | Basile | |
| 9,636,525 B1 | 5/2017 | Sahadevan | |
| 9,649,298 B2 | 5/2017 | Djonov et al. | |
| 9,656,098 B2 | 5/2017 | Goer | |
| 9,694,204 B2 | 7/2017 | Hardemark | |
| 9,776,017 B2 | 10/2017 | Flynn et al. | |
| 9,786,054 B2 | 10/2017 | Taguchi et al. | |
| 9,786,093 B2 | 10/2017 | Svensson | |
| 9,786,465 B2 | 10/2017 | Li et al. | |
| 9,795,806 B2 | 10/2017 | Matsuzaki et al. | |
| 9,801,594 B2 | 10/2017 | Boyd et al. | |
| 9,844,358 B2 | 12/2017 | Wiggers et al. | |
| 9,854,662 B2 | 12/2017 | Mishin | |
| 9,884,206 B2 * | 2/2018 | Schulte | A61N 5/103 |
| 9,925,382 B2 * | 3/2018 | Carlton | A61N 1/36128 |
| 9,931,522 B2 | 4/2018 | Bharadwaj et al. | |
| 9,962,562 B2 | 5/2018 | Fahrig et al. | |
| 9,974,977 B2 | 5/2018 | Lachaine et al. | |
| 9,987,502 B1 | 6/2018 | Gattiker et al. | |
| 10,007,961 B2 | 6/2018 | Grudzinski et al. | |
| 10,016,623 B2 * | 7/2018 | Claereboudt | H05H 7/04 |
| 10,022,564 B2 | 7/2018 | Thieme et al. | |
| 10,071,264 B2 | 9/2018 | Liger | |
| 10,080,912 B2 | 9/2018 | Kwak et al. | |
| 10,092,774 B1 | 10/2018 | Vanderstraten et al. | |
| 10,183,179 B1 | 1/2019 | Smith et al. | |
| 10,188,875 B2 | 1/2019 | Kwak et al. | |
| 10,206,871 B2 | 2/2019 | Lin et al. | |
| 10,212,800 B2 | 2/2019 | Agustsson et al. | |
| 10,232,193 B2 | 3/2019 | Iseki | |
| 10,258,810 B2 | 4/2019 | Zwart et al. | |
| 10,272,264 B2 | 4/2019 | Ollila et al. | |
| 10,279,196 B2 | 5/2019 | West et al. | |
| 10,293,184 B2 | 5/2019 | Pishdad et al. | |
| 10,307,614 B2 | 6/2019 | Schnarr | |
| 10,307,615 B2 | 6/2019 | Ollila et al. | |
| 10,315,047 B2 | 6/2019 | Glimelius et al. | |
| 10,413,755 B1 | 9/2019 | Sahadevan | |
| 10,449,389 B2 | 10/2019 | Ollila et al. | |
| 10,449,391 B2 * | 10/2019 | Buchsbaum | A61N 5/1067 |
| 10,485,988 B2 | 11/2019 | Kuusela et al. | |
| 10,525,285 B1 | 1/2020 | Friedman | |
| 10,549,117 B2 | 2/2020 | Vanderstraten et al. | |
| 10,603,514 B2 | 3/2020 | Grittani et al. | |
| 10,609,806 B2 | 3/2020 | Roecken et al. | |
| 10,610,700 B2 * | 4/2020 | Traneus | A61N 5/103 |
| 10,617,892 B2 * | 4/2020 | Oldham | A61N 5/103 |
| 10,636,609 B1 | 4/2020 | Bertsche et al. | |
| 10,660,588 B2 | 5/2020 | Boyd et al. | |
| 10,661,100 B2 | 5/2020 | Shen | |
| 10,682,528 B2 | 6/2020 | Ansorge et al. | |
| 10,702,716 B2 | 7/2020 | Heese | |
| 10,758,746 B2 | 9/2020 | Kwak et al. | |
| 10,814,144 B2 * | 10/2020 | Khuntia | A61N 5/103 |
| 10,870,018 B2 | 12/2020 | Bartkoski et al. | |
| 10,918,886 B2 * | 2/2021 | Smith | A61N 5/103 |
| 11,090,508 B2 * | 8/2021 | Folkerts | G16H 20/40 |
| 11,116,995 B2 * | 9/2021 | Khuntia | A61N 5/1031 |
| 11,173,325 B2 * | 11/2021 | Parry | A61K 33/242 |
| 2007/0287878 A1 | 12/2007 | Fantini et al. | |
| 2008/0023644 A1 | 1/2008 | Pedroni | |
| 2009/0063110 A1 | 3/2009 | Failla et al. | |
| 2009/0287467 A1 | 11/2009 | Sparks et al. | |
| 2010/0119032 A1 | 5/2010 | Yan et al. | |
| 2010/0177870 A1 | 7/2010 | Nord et al. | |
| 2010/0178245 A1 | 7/2010 | Arnsdorf et al. | |
| 2010/0260317 A1 | 10/2010 | Chang et al. | |
| 2011/0006224 A1 | 1/2011 | Maltz et al. | |
| 2011/0091015 A1 | 4/2011 | Yu et al. | |
| 2011/0135058 A1 | 6/2011 | Sgouros et al. | |
| 2012/0076271 A1 | 3/2012 | Yan et al. | |
| 2012/0157746 A1 | 6/2012 | Meltsner et al. | |
| 2012/0171745 A1 | 7/2012 | Itoh | |
| 2012/0197058 A1 | 8/2012 | Shukla et al. | |
| 2013/0116929 A1 | 5/2013 | Carlton et al. | |
| 2013/0150922 A1 | 6/2013 | Butson et al. | |
| 2013/0177641 A1 | 7/2013 | Ghoroghchian | |
| 2013/0231516 A1 | 9/2013 | Loo et al. | |
| 2014/0177807 A1 | 6/2014 | Lewellen et al. | |
| 2014/0185776 A1 | 7/2014 | Li et al. | |
| 2014/0206926 A1 | 7/2014 | van der Laarse | |

(56) References Cited

U.S. PATENT DOCUMENTS

| | | |
|---|---|---|
| 2014/0275706 A1 | 9/2014 | Dean et al. |
| 2014/0369476 A1 | 12/2014 | Harding |
| 2015/0011817 A1 | 1/2015 | Feng |
| 2015/0202464 A1 | 7/2015 | Brand et al. |
| 2015/0306423 A1 | 10/2015 | Bharat et al. |
| 2016/0279444 A1 | 9/2016 | Schlosser |
| 2016/0310764 A1 | 10/2016 | Bharadwaj et al. |
| 2017/0189721 A1 | 7/2017 | Sumanaweera et al. |
| 2017/0203129 A1 | 7/2017 | Dessy |
| 2017/0281973 A1 | 10/2017 | Allen et al. |
| 2018/0021594 A1 | 1/2018 | Papp et al. |
| 2018/0043183 A1 | 2/2018 | Sheng et al. |
| 2018/0056090 A1 | 3/2018 | Jordan et al. |
| 2018/0099154 A1 | 4/2018 | Prieels |
| 2018/0099155 A1 | 4/2018 | Prieels et al. |
| 2018/0099159 A1 | 4/2018 | Forton et al. |
| 2018/0154183 A1 | 6/2018 | Sahadevan |
| 2018/0197303 A1 | 7/2018 | Jordan et al. |
| 2018/0207425 A1 | 7/2018 | Carlton et al. |
| 2018/0236268 A1 | 8/2018 | Zwart et al. |
| 2019/0022407 A1 | 1/2019 | Abel et al. |
| 2019/0022422 A1 | 1/2019 | Trail et al. |
| 2019/0054315 A1 | 2/2019 | Isola et al. |
| 2019/0070435 A1 | 3/2019 | Joe Anto et al. |
| 2019/0168027 A1 | 6/2019 | Smith et al. |
| 2019/0255361 A1 | 8/2019 | Mansfield |
| 2019/0299027 A1 | 10/2019 | Fujii et al. |
| 2019/0299029 A1 | 10/2019 | Inoue |
| 2019/0351259 A1 | 11/2019 | Lee et al. |
| 2020/0001118 A1 | 1/2020 | Snider, III et al. |
| 2020/0022248 A1 | 1/2020 | Yi et al. |
| 2020/0030633 A1 | 1/2020 | Van Heteren et al. |
| 2020/0035438 A1 | 1/2020 | Star-Lack et al. |
| 2020/0069818 A1 | 3/2020 | Jaskula-Ranga et al. |
| 2020/0164224 A1 | 5/2020 | Vanderstraten et al. |
| 2020/0178890 A1 | 6/2020 | Otto |
| 2020/0197730 A1 | 6/2020 | Safavi-Naeini et al. |
| 2020/0254279 A1 | 8/2020 | Ohishi |
| 2020/0269068 A1 | 8/2020 | Abel et al. |
| 2020/0276456 A1 | 9/2020 | Swerdloff |
| 2020/0282234 A1 | 9/2020 | Folkerts et al. |

FOREIGN PATENT DOCUMENTS

| | | |
|---|---|---|
| CN | 107362464 | 11/2017 |
| CN | 109966662 | 7/2019 |
| CN | 111481840 | 8/2020 |
| CN | 111481841 | 8/2020 |
| EA | 010207 | 6/2008 |
| EP | 0979656 | 2/2000 |
| EP | 3178522 | 6/2017 |
| EP | 3338858 | 6/2018 |
| EP | 3384961 | 10/2018 |
| EP | 3421087 | 1/2019 |
| EP | 3453427 | 3/2019 |
| EP | 3586920 | 1/2020 |
| JP | 2617283 | 6/1997 |
| JP | 2019097969 | 6/2019 |
| WO | 2007017177 | 2/2007 |
| WO | 2010018476 | 2/2010 |
| WO | 2013081218 | 6/2013 |
| WO | 2013133936 | 9/2013 |
| WO | 2014139493 | 9/2014 |
| WO | 2015038832 | 3/2015 |
| WO | 2015102680 | 7/2015 |
| WO | 2016122957 | 8/2016 |
| WO | 2017156316 | 9/2017 |
| WO | 2017174643 | 10/2017 |
| WO | 2018137772 | 8/2018 |
| WO | 2018152302 | 8/2018 |
| WO | 2019097250 | 5/2019 |
| WO | 2019103983 | 5/2019 |
| WO | 2019164835 | 8/2019 |
| WO | 2019166702 | 9/2019 |
| WO | 2019185378 | 10/2019 |
| WO | 2019222436 | 11/2019 |
| WO | 2020018904 | 1/2020 |
| WO | 2020064832 | 4/2020 |
| WO | 2020107121 | 6/2020 |
| WO | 2020159360 | 8/2020 |

OTHER PUBLICATIONS

Greg Schimke et al., A Model for Secondary Monitor Unit Calculations of PBS Proton Therapy Treatment Plans, International Journal of Particle Therapy 5(3): 5-10 (2019). (Year: 2019).*

Sheng Huang et al., Validation and clinical implementation of an accurate Monte Carlo code for pencil beam scanning proton therapy, Journal of Applied Clinical Medical Physics 19(5): 558-572, (2018). (Year: 2018).*

Liyong Lin et al., Beam-specific planning target volumes incorporating 4D CT for pencil beam scanning proton therapy of thoracic tumors, Journal of Applied Clinical Medical Physics, 16(6), 281-292 (2015). (Year: 2015).*

X. Ronald Zhu et al., Towards Effective and Efficient Patient-Specific Quality Assurance for Spot Scanning Proton Therapy, Cancers 7(2): 631-647 (2015). (Year: 2015).*

Martin Hillbrand and Dietmar Georg, Assessing a set of optimal user interface parameters for intensity-modulated proton therapy planning, Journal of Applied Clinical Medical Physics, vol. 11, No. 4, 93-104 (2010). (Year: 2010).*

M. McManus et al., "The challenge of ionisation chamber dosimetry in ultra-short pulsed high dose-rate Very High Energy Electron beams," Sci Rep 10, 9089 (2020), published Jun. 3, 2020, https://doi.org/10.1038/s41598-020-65819-y.

Ibrahim Oraiqat et al., "An Ionizing Radiation Acoustic Imaging (iRAI) Technique for Real-Time Dosimetric Measurements for FLASH Radiotherapy," Medical Physics, vol. 47, Issue10, Oct. 2020, pp. 5090-5101, First published: Jun. 27, 2020, https://doi.org/10.1002/mp.14358.

K. Petersson et al., "Dosimetry of ultra high dose rate irradiation for studies on the biological effect induced in normal brain and GBM," ICTR-PHE 2016, p. S84, Feb. 2016, https://publisher-connector.core.ac.uk/resourcesync/data/elsevier/pdf/14c/aHR0cDovL2FwaS5 lbHNldmllci5jb20vY29udGVudC9hcnRpY2xlL3BpaS9zMDE2Nz gxNDAxNjMwMTcyNA==.pdf.

Susanne Auer et al., "Survival of tumor cells after proton irradiation with ultra-high dose rates," Radiation Oncology 2011, 6:139, Published Oct. 18, 2011, DOI: https://doi.org/10.1186/1748-717X-6-139.

Cynthia E. Keen, "Clinical linear accelerator delivers FLASH radiotherapy," Physics World, Apr. 23, 2019, IOP Publishing Ltd, https://physicsworld.com/a/clinical-linear-accelerator-delivers-flash-radiotherapy/.

Fan et al., "Emission guided radiation therapy for lung and prostate cancers: A feasibility study on a digital patient," Med Phys. Nov. 2012; 39(11): 7140-7152. Published online Nov. 5, 2012. https://www.ncbi.nlm.nih.gov/pmc/articles/PMC3505203/ doi: 10.1118/1.4761951.

Favaudon et al., "Ultrahigh dose-rate, "flash" irradiation minimizes the side-effects of radiotherapy," Cancer / Radiotherapy, vol. 19, Issues 6-7 , Oct. 2015 , pp. 526-531, Available online Aug. 12, 2015, https://doi.org/10.1016/j.canrad.2015.04.006.

O. Zlobinskaya et al., "The Effects of Ultra-High Dose Rate Proton Irradiation on Growth Delay in the Treatment of Human Tumor Xenografts in Nude Mice," Radiation Research, 181(2):177-183. Published Feb. 13, 2014, DOI: http://dx.doi.org/10.1667/RR13464.1.

Bjorn Zackrisson, "Biological Effects Of High Energy Radiation And Ultra High Dose Rates," Umea University Medical Dissertations, New series No. 315—ISSN 0346-6612, From the Department of Oncology, University of Umea, Umea, Sweden, ISBN 91-7174-614-5, Printed in Sweden by the Printing Office of Umea University, Umea, 1991.

P. Montay-Gruel et al., "Irradiation in a flash: Unique sparing of memory in mice after whole brain irradiation with dose rates above

(56) References Cited

OTHER PUBLICATIONS

100 Gy/s," Radiotherapy and Oncology, vol. 124, Issue 3, Sep. 2017, pp. 365-369, Available online May 22, 2017, doi: 10.1016/j.radonc.2017.05.003.

BW Loo et al., "Delivery of Ultra-Rapid Flash Radiation Therapy and Demonstration of Normal Tissue Sparing After Abdominal Irradiation of Mice," International Journal of Radiation Oncology, Biology, Physics, vol. 98, Issue 2, p. E16, Supplement: S Meeting Abstract: P003, Published: Jun. 1, 2017, DOI: https://doi.org/10.1016/j.ijrobp.2017.02.101.

Bhanu Prasad Venkatesulu et al., "Ultra high dose rate (35 Gy/sec) radiation does not spare the normal tissue in cardiac and splenic models of lymphopenia and gastrointestinal syndrome," Sci Rep 9, 17180 (2019), Published Nov. 20, 2019, DOI: https://doi.org/10.1038/s41598-019-53562-y.

P. Montay-Gruel et al., "Long-term neurocognitive benefits of FLASH radiotherapy driven by reduced reactive oxygen species," PNAS May 28, 2019, vol. 116, No. 22, pp. 10943-10951; first published May 16, 2019, https://doi.org/10.1073/pnas.1901777116.

Peter G. Maxim et al., "FLASH radiotherapy: Newsflash or flash in the pan?", Medical Physics, 46 (10), Oct. 2019, pp. 4287-4290, American Association of Physicists in Medicine, First published: Jun. 27, 2019, https://doi.org/10.1002/mp.13685.

Andrei Pugachev et al., "Pseudo beam's-eye-view as applied to beam orientation selection in intensity-modulated radiation therapy," Int. J. Radiation Oncology Biol. Phys., vol. 51, Issue 5, p. 1361-1370, Dec. 1, 2001, DOI: https://doi.org/10.1016/S0360-3016(01)01736-9.

Xiaodong Zhang et al., "Intensity-Modulated Proton Therapy Reduces the Dose to Normal Tissue Compared With Intensity-Modulated Radiation Therapy or Passive Scattering Proton Therapy and Enables Individualized Radical Radiotherapy for Extensive Stage IIIB Non-Small-Cell Lung Cancer: A Virtual Clinical Study," Int. J. Radiation Oncology Biol. Phys., vol. 77, No. 2, pp. 357-366, 2010, Available online Aug. 5, 2009, DOI: https://doi.org/10.1016/j.ijrobp.2009.04.028.

A. J. Lomax et al, "Intensity modulated proton therapy: A clinical example," Medical Physics, vol. 28, Issue 3, Mar. 2001, pp. 317-324, First published: Mar. 9, 2001, https://doi.org/10.1118/1.1350587.

Lamberto Widesott et al., "Intensity-Modulated Proton Therapy Versus Helical Tomotherapy in Nasopharynx Cancer: Planning Comparison and NTCP Evaluation," Int. J. Radiation Oncology Biol. Phys., vol. 72, No. 2, pp. 589-596, Oct. 1, 2008, Available online Sep. 13, 2008, DOI: https://doi.org/10.1016/j.ijrobp.2008.05.065.

Andrei Pugachev et al., "Role of beam orientation optimization in intensity-modulated radiation therapy," Int. J. Radiation Oncology Biol. Phys., vol. 50, No. 2, pp. 551-560, Jun. 1, 2001, Available online May 10, 2001, DOI: https://doi.org/10.1016/S0360-3016(01)01502-4.

Damien C. Weber et al., "Radiation therapy planning with photons and protons for early and advanced breast cancer: an overview," Radiat Oncol. 2006; 1: 22. Published online Jul. 20, 2006, doi: 10.1186/1748-717X-1-22.

RaySearch Laboratories, "Leading the way in cancer treatment, Annual Report 2013," RaySearch Laboratories (publ), Stockholm, Sweden, 94 pages, Apr. 2014, https://www.raysearchlabs.com/siteassets/about-overview/media-center/wp-re-ev-n-pdfs/brochures/raysearch-ar-2013-eng.pdf.

Fredrik Carlsson, "Utilizing Problem Structure in Optimization of Radiation Therapy," KTH Engineering Sciences, Doctoral Thesis, Stockholm, Sweden, Apr. 2008, Optimization and Systems Theory, Department of Mathematics, Royal Institute of Technology, Stockholm, Sweden, ISSN 1401-2294, https://www.raysearchlabs.com/globalassets/about-overview/media-center/wp-re-ev-n-pdfs/publications/thesis-fredrik_light.pdf.

Chang-Ming Charlie Ma, "Physics and Dosimetric Principles of SRS and SBRT," Mathews J Cancer Sci. 4(2): 22, 2019, published: Dec. 11, 2019, ISSN: 2474-6797, DOI: https://doi.org/10.30654/MJCS.10022.

Alterego-Admin, "Conventional Radiation Therapy May Not Protect Healthy Brain Cells," International Neuropsychiatric Association—INA, Oct. 10, 2019, https://inawebsite.org/conventional-radiation-therapy-may-not-protect-healthy-brain-cells/.

Aafke Christine Kraan, "Range verification methods in particle therapy: underlying physics and Monte Carlo modeling," Frontiers in Oncology, Jul. 7, 2015, vol. 5, Article 150, 27 pages, doi: 10.3389/fonc.2015.00150.

Wayne D. Newhauser et al., "The physics of proton therapy," Physics in Medicine & Biology, Mar. 24, 2015, 60 R155-R209, Institute of Physics and Engineering in Medicine, IOP Publishing, doi: 10.1088/0031-9155/60/8/R155.

S E McGowan et al., "Treatment planning optimisation in proton therapy," Br J Radiol, 2013, 86, 20120288, The British Institute of Radiology, 12 pages, DOI: 10.1259.bjr.20120288.

Steven Van De Water et al., "Towards FLASH proton therapy: the impact of treatment planning and machine characteristics on achievable dose rates," ACTA Oncologica, Jun. 26, 2019, vol. 58, No. 10, p. 1462-1469, Taylor & Francis Group, DOI: 10.1080/0284186X.2019.1627416.

J. Groen, "FLASH optimisation in clinical IMPT treatment planning," MSc Thesis, Jul. 1, 2020, Erasmus University Medical Center, department of radiotherapy, Delft University of Technology, 72 pages.

Muhammad Ramish Ashraf et al., "Dosimetry for FLASH Radiotherapy: A Review of Tools and the Role of Radioluminescence and Cherenkov Emission," Frontiers in Oncology, Aug. 21, 2020, vol. 8, Article 328, 20 pages, doi: 10.3389/fphy.2020.00328.

Emil Schuler et al., "Experimental Platform for Ultra-high Dose Rate FLASH Irradiation of Small Animals Using a Clinical Linear Accelerator," International Journal of Radiation Oncology, Biology, Physics, vol. 97, No. 1, Sep. 2016, pp. 195-203.

Elette Engels et al., "Toward personalized synchrotron microbeam radiation therapy," Scientific Reports, 10:8833, Jun. 1, 2020, 13 pages, DOI: https://doi.org/10.1038/s41598-020-65729-z.

P-H Mackeprang et al., "Assessing dose rate distributions in VMAT plans" (Accepted Version), Accepted Version: https://boris.unibe.ch/92814/8/dose_rate_project_revised_submit.pdf Published Version: 2016, Physics in medicine and biology, 61(8), pp. 3208-3221. Institute of Physics Publishing IOP, published Mar. 29, 2016, https://boris.unibe.ch/92814/.

Xiaoying Liang et al., "Using Robust Optimization for Skin Flashing in Intensity Modulated Radiation Therapy for Breast Cancer Treatment: A Feasibility Study," Practical Radiation Oncology, vol. 10, Issue 1, p. 59-69, Published by Elsevier Inc., Oct. 15, 2019.

Alexei Trofimov et al., "Optimization of Beam Parameters and Treatment Planning for Intensity Modulated Proton Therapy," Technology in Cancer Research & Treatment, vol. 2, No. 5, Oct. 2003, p. 437-444, Adenine Press.

Vladimir Anferov, "Scan pattern optimization for uniform proton beam scanning," Medical Physics, vol. 36, Issue 8, Aug. 2009, pp. 3560-3567, First published: Jul. 2, 2009.

Ryosuke Kohno et al., "Development of Continuous Line Scanning System Prototype for Proton Beam Therapy," International Journal of Particle Therapy, Jul. 11, 2017, vol. 3, Issue 4, p. 429-438, DOI: 10.14338/IJPT-16-00017.1.

Wenbo Gu et al., "Integrated Beam Orientation and Scanning-Spot Optimization in Intensity Modulated Proton Therapy for Brain and Unilateral Head and Neck Tumors," Med Phys. Author manuscript; available in PMC Apr. 1, 2019. https://www.ncbi.nlm.nih.gov/pmc/articles/PMC5904040/ Published in final edited form as: Med Phys. Apr. 2018; 45(4): 1338-1350. Published online Mar. 1, 2018. doi: 10.1002/mp.12788 Accepted manuscript online: Feb. 2, 2018.

Paul Morel et al., "Spot weight adaptation for moving target in spot scanning proton therapy," Frontiers in Oncology, May 28, 2015, vol. 5, Article 119, 7 pages, doi: 10.3389/fonc.2015.00119.

Simeon Nill et al., "Inverse planning of intensity modulated proton therapy," Zeitschrift fur Medizinische Physik, vol. 14, Issue 1, 2004, pp. 35-40, https://doi.org/10.1078/0939-3889-00198.

(56) References Cited

OTHER PUBLICATIONS

A. Lomax, "Intensity modulation methods for proton radiotherapy," Physics in Medicine & Biology, Jan. 1999, vol. 44, No. 1, pp. 185-205, doi: 10.1088/0031-9155/44/1/014.

M Kramer et al., "Treatment planning for heavy-ion radiotherapy: physical beam model and dose optimization," Physics in Medicine & Biology, 2000, vol. 45, No. 11, pp. 3299-3317, doi: 10.1088/0031-9155/45/11/313.

Harald Paganetti, "Proton Beam Therapy," Jan. 2017, Physics World Discovery, IOP Publishing Ltd, Bristol, UK, 34 pages, DOI: 10.1088/978-0-7503-1370-4.

Shinichi Shimizu et al., "A Proton Beam Therapy System Dedicated to Spot-Scanning Increases Accuracy with Moving Tumors by Real-Time Imaging and Gating and Reduces Equipment Size," PLoS ONE, Apr. 18, 2014, vol. 9, Issue 4, e94971, https://doi.org/10.1371/journal.pone.0094971.

Heng Li et al., "Reducing Dose Uncertainty for Spot-Scanning Proton Beam Therapy of Moving Tumors by Optimizing the Spot Delivery Sequence," International Journal of Radiation Oncology, Biology, Physics, vol. 93, Issue 3, Nov. 1, 2015, pp. 547-556, available online Jun. 18, 2015, https://doi.org/10.1016/j.ijrobp.2015.06.019.

Ion Beam Applications SA, "Netherlands Proton Therapy Center Delivers First Clinical Flash Irradiation," Imaging Technology News, May 2, 2019, Wainscot Media, https://www.itnonline.com/content/netherlands-proton-therapy-center-delivers-first-clinical-flash-irradiation.

R. M. De Kruijff, "FLASH radiotherapy: ultra-high dose rates to spare healthy tissue," International Journal of Radiation Biology, 2020, vol. 96, No. 4, pp. 419-423, published online: Dec. 19, 2019, https://doi.org/10.1080/09553002.2020.1704912.

Mevion Medical Systems, "Focus On The Future: Flash Therapy," Press Releases, Sep. 16, 2019, https://www.mevion.com/newsroom/press-releases/focus-future-flash-therapy.

Joseph D. Wilson et al., "Ultra-High Dose Rate (FLASH) Radiotherapy: Silver Bullet or Fool's Gold?", Frontiers in Oncology, Jan. 17, 2020, vol. 9, Article 1563, 12 pages, doi: 10.3389/fonc.2019.01563.

David P. Gierga, "Is Flash Radiotherapy coming?", International Organization for Medical Physics, 2020, https://www.iomp.org/iomp-news2-flash-radiotherapy/.

Abdullah Muhammad Zakaria et al., "Ultra-High Dose-Rate, Pulsed (FLASH) Radiotherapy with Carbon Ions: Generation of Early, Transient, Highly Oxygenated Conditions in the Tumor Environment," Radiation Research, Dec. 1, 2020, vol. 194, Issue 6, pp. 587-593, Radiation Research Society, Published: Aug. 27, 2020, doi: https://doi.org/10.1667/RADE-19-00015.1.

Yusuke Demizu et al., "Carbon Ion Therapy for Early-Stage Non-Small-Cell Lung Cancer," BioMed Research International, vol. 2014, Article ID 727962, 9 pages, Hindawi Publishing Corporation, published: Sep. 11, 2014, https://doi.org/10.1155/2014/727962.

Ivana Dokic et al., "Next generation multi-scale biophysical characterization of high precision cancer particle radiotherapy using clinical proton, helium-, carbon- and oxygen ion beams," Oncotarget, Aug. 30, 2016, vol. 7, No. 35, pp. 56676-56689, published online: Aug. 1, 2016, doi: 10.18632/oncotarget.10996.

Aetna Inc., "Proton Beam, Neutron Beam, and Carbon Ion Radiotherapy," 2020, No. 0270, http://www.aetna.com/cpb/medical/data/200_299/0270.html.

Nicholas W. Colangelo et al., "The Importance and Clinical Implications of FLASH Ultra-High Dose-Rate Studies for Proton and Heavy Ion Radiotherapy," Radiat Res. Author manuscript; available in PMC Jan. 1, 2021. https://www.ncbi.nlm.nih.gov/pmc/articles/PMC6949397/ Published in final edited form as: Radiat Res. Jan. 2020; 193(1): 1-4. Published online Oct. 28, 2019. doi: 10.1667/RR15537.1.

Vincent Favaudon et al., "Ultrahigh dose-rate FLASH irradiation increases the differential response between normal and tumor tissue in mice," Science Translational Medicine, Jul. 16, 2014, vol. 6, Issue 245, 245ra93, American Association for the Advancement of Science, DOI: 10.1126/scitranslmed.3008973.

"FlashRad: Ultra-high dose-rate Flash radiotherapy to minimize the complications of radiotherapy," 2014, https://siric.curie.fr/sites/default/files/atoms/files/flashrad.pdf.

Tami Freeman, "FLASH radiotherapy: from preclinical promise to the first human treatment," Physics World, Aug. 6, 2019, IOP Publishing Ltd, https://physicsworld.com/a/flash-radiotherapy-from-preclinical-promise-to-the-first-human-treatment/.

IntraOp Medical, Inc., "IntraOp and Lausanne University Hospital Announce Collaboration in FLASH radiotherapy," Jun. 18, 2020, https://intraop.com/news-events/lausanne-university-flash-radiotherapy-collaboration/.

M.-C. Vozenin et al., "Biological Benefits of Ultra-high Dose Rate FLASH Radiotherapy: Sleeping Beauty Awoken," Clin Oncol (R Coll Radiol). Author manuscript; available in PMC Nov. 12, 2019. https://www.ncbi.nlm.nih.gov/pmc/articles/PMC6850216/ Published in final edited form as: Clin Oncol (R Coll Radiol). Jul. 2019; 31(7): 407-415. Published online Apr. 19, 2019. doi: 10.1016/j.clon.2019.04.001.

Efstathios Kamperis et al., "A FLASH back to radiotherapy's past and then fast forward to the future," J Cancer Prev Curr Res. 2019;10(6):142-144. published Nov. 13, 2019, DOI: 10.15406/jcpcr.2019.10.00407.

P. Symonds et al., "FLASH Radiotherapy: The Next Technological Advance in Radiation Therapy?", Clinical Oncology, vol. 31, Issue 7, p. 405-406, Jul. 1, 2019, The Royal College of Radiologists, Published by Elsevier Ltd., DOI: https://doi.org/10.1016/j.clon.2019.05.011.

Swati Girdhani et al., "Abstract LB-280: FLASH: A novel paradigm changing tumor irradiation platform that enhances therapeutic ratio by reducing normal tissue toxicity and activating immune pathways," Proceedings: AACR Annual Meeting 2019; Mar. 29-Apr. 3, 2019; Atlanta, GA, published Jul. 2019, vol. 79, Issue 13 Supplement, pp. LB-280, American Association for Cancer Research, DOI: https://doi.org/10.1158/1538-7445.AM2019-LB-280.

Bazalova-Carter et al., "On the capabilities of conventional x-ray tubes to deliver ultra-high (FLASH) dose rates," Med. Phys. Dec. 2019; 46 (12):5690-5695, published Oct. 23, 2019, American Association of Physicists in Medicine, doi: 10.1002/mp.13858. Epub Oct. 23, 2019. PMID: 31600830.

Manuela Buonanno et al., "Biological effects in normal cells exposed to FLASH dose rate protons," Radiother Oncol. Author manuscript; available in PMC Oct. 1, 2020. https://www.ncbi.nlm.nih.gov/pmc/articles/PMC6728238/ Published in final edited form as: Radiother Oncol. Oct. 2019; 139: 51-55. Published online Mar. 5, 2019. doi: 10.1016/j.radonc.2019.02.009.

N. Rama et al., "Improved Tumor Control Through T-cell Infiltration Modulated by Ultra-High Dose Rate Proton FLASH Using a Clinical Pencil Beam Scanning Proton System," International Journal of Radiation Oncology, Biology, Physics, vol. 105, Issue 1, Supplement , S164-S165, Sep. 1, 2019, Mini Oral Sessions, DOI: https://doi.org/10.1016/j.ijrobp.2019.06.187.

INSERM Press Office, "Radiotherapy 'flashes' to reduce side effects," Press Release, Jul. 16, 2014, https://presse.inserm.fr/en/radiotherapy-flashes-to-reduce-side-effects/13394/.

Eric S. Diffenderfer et al., "Design, Implementation, and in Vivo Validation of a Novel Proton FLASH Radiation Therapy System," International Journal of Radiation Oncology, Biology, Physics, vol. 106, Issue 2, Feb. 1, 2020, pp. 440-448, Available online Jan. 9, 2020, Published by Elsevier Inc., DOI: https://doi.org/10.1016/j.ijrobp.2019.10.049.

Valerie Devillaine, "Radiotherapy and Radiation Biology," Institut Curie, Apr. 21, 2017, https://institut-curie.org/page/radiotherapy-and-radiation-biology.

Imaging Technology News, "ProNova and medPhoton to Offer Next Generation Beam Delivery, Advanced Imaging for Proton Therapy," Oct. 6, 2014, Wainscot Media, Link: https://www.itnonline.com/content/pronova-and-medphoton-offer-next-generation-beam-delivery-advanced-imaging-proton-therapy.

Oncolink Team, "Radiation Therapy: Which type is right for me?", OncoLink Penn Medicine, last reviewed Mar. 3, 2020, Trustees of

(56) References Cited

OTHER PUBLICATIONS the University of Pennsylvania, https://www.oncolink.org/cancer-treatment/radiation/introduction-to-radiation-therapy/radiation-therapy-which-type-is-right-for-me.

Marco Durante et al., "Faster and safer? FLASH ultra-high dose rate in radiotherapy," Br J Radiol 2018; 91(1082): Jun. 28, 2017, British Institute of Radiology, Published Online: Dec. 15, 2017, https://doi.org/10.1259/bjr.20170628.

John R. Fischer, "PMB launches FLASH radiotherapy system for use in clinical trials," Healthcare Business News, Jun. 29, 2020, DOTmed.com, Inc., https://www.dotmed.com/news/story/51662.

Marie-Catherine Vozenin et al., "The advantage of FLASH radiotherapy confirmed in mini-pig and cat-cancer patients," Clinical Cancer Research, Author Manuscript Published OnlineFirst Jun. 6, 2018, https://clincancerres.aacrjournals.org/content/clincanres/early/2018/06/06/1078-0432.CCR-17-3375.full.pdf.

Van Marlen Patricia et al: "Bringing FLASH to the Clinic:Treatment Planning Consideration for Ultrahigh Dose-Rate Proton Beams" International Journal of Radiation:Oncology Biology Physics, Pergamon Press, USA, vol. 106, No. 3, Nov. 20, 2019 (Nov. 20, 2019), pp. 621-629, XP086013111, ISSN: 0360-3016, DOI: 10.1016/J.IJROBP.2019.11.011 (Retrieved on Nov. 20, 2019) pp. 623, right-hand column.

Folkerts Michael M et al: "A Framework for Defining FLASH dose rate for pencil beam scanning." Medical Physics, vol. 47, No. 12, Dec. 2020 (Dec. 2020), pp. 6396-6404, XP002804313, issn: 2473-4209, DOI: 10.1002/mp.14456 Chapter 2.

\* cited by examiner

DEFINING DOSE RATE FOR PENCIL BEAM SCANNING

BACKGROUND

The use of radiation therapy to treat cancer is well known. Typically, radiation therapy involves directing a beam of high energy proton, photon, ion, or electron radiation into a target or volume in a treatment target of unhealthy tissue (e.g., a tumor or lesion).

Radiation therapy using proton beams has a significant advantage relative to the use of other types of beams. A proton beam reaches a depth in tissue that depends on the energy of the beam, and releases most of its energy (delivers most of its dose) at that depth. The region of a depth-dose curve where most of the energy is released is referred to as the Bragg peak of the beam.

Before a patient is treated with radiation, a treatment plan specific to that patient is developed. The plan defines various aspects of the radiation therapy using simulations and optimizations that may be based on past experiences. In general, the purpose of the treatment plan is to deliver sufficient radiation to unhealthy tissue while minimizing exposure of surrounding healthy tissue to that radiation.

One radiation therapy technique is known as pencil beam scanning (PBS), also known as spot scanning. In PBS, a small and focused pencil beam of ionizing radiation is directed to specific locations (spots) in a treatment target prescribed by the treatment plan. The prescribed spot positions are typically arranged in a fixed (raster) pattern for each energy layer of the treatment field, and the pencil beam is delivered on a fixed scanning path within an energy layer. By superposition of several layers of different energies, the Bragg peaks of the pencil beams overlap to uniformly deliver the prescribed dose at a prescribed dose rate across each treatment field in the treatment target and up to the edges of the target.

A precise calculation of the number of spots and their placement (location and distribution) is critical. The goal is to determine a spot placement that: 1) conforms to the outline of the treatment target, to improve the lateral penumbra and spare healthy tissue outside the treatment target from exposure to radiation beyond what is necessary to treat the unhealthy tissue; and 2) is uniform inside the treatment target, to avoid dose variations (dose inhomogeneity) inside the treatment target so that the prescribed dose is delivered to all parts of the target.

The interest in the biological effects of ultra-high dose rate irradiation has grown significantly in the last half-decade, starting with studies showing that significant sparing of normal tissue with isoeffective tumor growth delay was demonstrated through irradiation at dose rates on the order of 40 Gray (Gy) per second. That sparing effect, which is known as the FLASH effect, has resulted in a large number of radiobiology experiments, most of which have been performed using broad beams of electrons or protons (bb-FLASH). In these experiments, the dose is pulsed in the time domain, with delivery of the entire field happening simultaneously within each pulse. This mode of dose delivery has two characteristic dose rates. The first is the instantaneous dose rate, which is the dose per pulse divided by the pulse duration. The second is the average dose rate, which is the total dose divided by the entire delivery duration.

PBS introduces additional considerations for defining dose rate because, as mentioned above, the dose at each point in the treatment field is the sum of contributions from the dose delivered asynchronously to multiple spots that are close enough to that point to contribute to the dose at that point. While each spot will have instantaneous and average dose rates analogous to those discussed above for broad beams, the dose rate at any voxel within a PBS field is more difficult to characterize.

SUMMARY

For pencil beam scanning (PBS) (spot scanning) in general and PBS FLASH radiotherapy in particular, it is important to consider the scanning time. Without considering the scanning time, the temporal separation between spots delivering significant dose to a given location is not accounted for, and as a result the dose rate estimate for an array of spots will be the same regardless of the time period required to accumulate the total dose.

Embodiments according to the present invention provide methods and systems that consider dose accumulation in a local region or sub-volume (e.g., a voxel) as a function of time. More specifically, in embodiments, methods are disclosed for (i) calculating the dose rate of voxels within a particle beam (e.g., proton beam) treatment field delivered using PBS (in other words, the dose rate distribution of a PBS treatment field), and (ii) reporting a representative dose rate for the PBS treatment field.

The disclosed methods take into account the unique spatiotemporal delivery patterns of PBS FLASH radiotherapy. This provides a framework for determining and describing PBS dose rate in a precise and consistent manner, a necessary requirement for cross-investigational comparison of FLASH results. These methods can be used for radiation treatment planning as well as for advancing the research and application of PBS FLASH radiotherapy.

These and other objects and advantages of embodiments according to the present invention will be recognized by one skilled in the art after having read the following detailed description, which are illustrated in the various drawing figures.

This summary is provided to introduce a selection of concepts that are further described below in the detailed description that follows. This summary is not intended to identify key features or essential features of the claimed subject matter, nor is it intended to be used to limit the scope of the claimed subject matter.

BRIEF DESCRIPTION OF DRAWINGS

The accompanying drawings, which are incorporated in and form a part of this specification and in which like numerals depict like elements, illustrate embodiments of the present disclosure and, together with the detailed description, serve to explain the principles of the disclosure. The drawings are not necessarily drawn to scale.

The patent or application file contains at least one drawing executed in color. Copies of this patent or patent application publication with color drawing(s) will be provided by the Office upon request and payment of the necessary fee.

DETAILED DESCRIPTION

Figure 1:
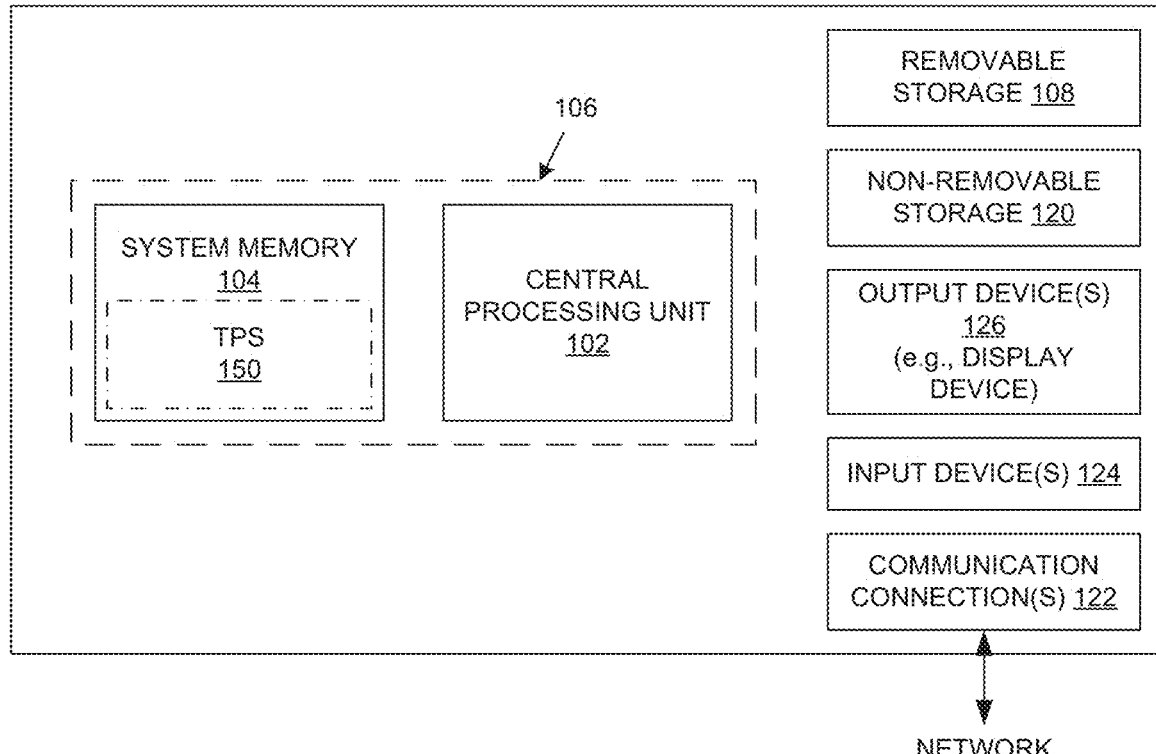
FIG. 1 is a block diagram of an example of a computer system upon which the embodiments described herein may be implemented.

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computer system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "accessing," "determining," "using," "storing," "performing," "associating," or the like, refer to actions and processes (e.g., the flowchart of FIG. 7) of a computer system or similar electronic computing device or processor (e.g., the computer system 100 of FIG. 1). The computer system or similar electronic computing device manipulates and transforms data represented as physical (electronic) quantities within the computer system memories, registers or other such information storage, transmission or display devices.

The discussion to follow may include terms such as "dose," "dose rate," "energy," etc. Unless otherwise noted, a value is associated with each such term. For example, a dose has a value and can have different values. For simplicity, the term "dose" may refer to a value of a dose, for example, unless otherwise noted or apparent from the discussion.

Portions of the detailed description that follows are presented and discussed in terms of methods. Although steps and sequencing thereof are disclosed in figures herein (e.g., FIG. 7) describing the operations of those methods, such steps and sequencing are examples only. Embodiments are well suited to performing various other steps or variations of the steps recited in the flowcharts of the figures herein, and in a sequence other than that depicted and described herein.

Embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory, read only memory (ROM), electrically erasable programmable ROM (EE-PROM), flash memory or other memory technology, compact disk ROM (CD-ROM), digital versatile disks (DVDs) or other optical or magnetic storage devices, or any other medium that can be used to store the desired information and that can accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared and other wireless media. Combinations of any of the above can also be included within the scope of computer-readable media.

FIG. 1 shows a block diagram of an example of a computer system 100 upon which the embodiments described herein may be implemented. In its most basic configuration, the computer system 100 includes at least one central processing unit 102 and system memory 104. This most basic configuration is illustrated in FIG. 1 by dashed line 106. The computer system 100 may also have additional features and/or functionality. For example, the computer system 100 may also include additional storage (removable and/or non-removable) including, but not limited to, magnetic or optical disks or tape. Such additional storage is illustrated in FIG. 1 by removable storage 108 and non-removable storage 120. The computer system 100 may also contain communications connection(s) 122 that allow the computer system 100 to communicate with other devices, e.g., in a networked environment using logical connections to one or more remote computers.

The computer system 100 also includes input device(s) 124 such as keyboard, mouse, pen, voice input device, touch input device, etc. Output device(s) 126 such as a display device, speakers, printer, etc., are also included. A display device may be, for example, a cathode ray tube display, a light-emitting diode display, or a liquid crystal display.

In the example of FIG. 1, the system memory 104 includes computer-readable instructions, data structures, program modules, and the like associated with a treatment planning system (TPS) 150. However, the treatment planning system 150 may instead reside in any one of the computer storage media used by the computer system 100, or may be distributed over some combination of the computer storage media, or may be distributed over some combination of networked computers. The treatment planning system 150 is used to evaluate and produce a final (prescribed) treatment plan. The treatment planning system 150 can also be used to perform the calculations and related operations described below.

A proposed radiation treatment plan is defined (e.g., using the treatment planning system 150 of FIG. 1), stored in a computer system memory, and accessed from that memory. The proposed radiation treatment plan includes values of parameters that can affect dose and dose rate, as well as other parameters. The parameters that can affect dose and dose rate include, but are not limited to, a number of irradiations of the volume in a treatment target, a duration of each of the irradiations (irradiation times), and a dose deposited in each of the irradiations. The parameters may also include angles (directions) of beams to be directed toward a treatment target, and a beam energy for each of the beams. Other parameters are mentioned above. The volume of a treatment target may be divided into sub-volumes or voxels, in which case the values of the parameters can be on a per-sub-volume or per-voxel basis (e.g., a value per sub-volume or voxel).

A control system (not shown) implemented with a computer system like the computer system of 100 can be used to implement the prescribed radiation treatment plan. The control system can control parameters of a beam-generating system, a nozzle, and a patient support device, including parameters such as the energy, intensity, direction, size, and/or shape of the beam, according to data it receives and according to the prescribed radiation treatment plan.

During treatment, in an example embodiment, a particle beam enters the nozzle, which includes one or more components that affect (e.g., decrease, modulate) the energy of the beam, to control the dose delivered by the beam and/or to control the depth versus dose curve of the beam, depending on the type of beam. For example, for a proton beam or an ion beam that has a Bragg peak, the nozzle can control the location of the Bragg peak in the treatment target.

In embodiments according to the invention, the nozzle emits particles in a spot scanning beam (also referred to as a pencil beam). The nozzle is mounted on a moveable gantry so that the beam can be delivered from different directions (angles) relative to a patient (treatment target) on the patient support device, and the position of the patient support device relative to the beam may also be changed. The target area is irradiated with a raster scan by the spot scanning beam. The increased flexibility made available through spot scanning greatly improves the precision of the dose delivered to a treatment, to maximize dose delivery to unhealthy tissue and minimize damage to healthy tissue.

The beam can deliver a relatively high dose rate (a relatively high dose in a relatively short period of time). For example, the beam can deliver at least 40 Gray (Gy) in less than one second, and may deliver as much as 120 Gy per second or more.

In radiation therapy techniques in which the intensity of the particle beam is either constant or modulated across the field of delivery, such as in intensity modulated radiation therapy (IMRT) and intensity modulated particle therapy (IMPT), beam intensity is varied across each treatment region (volume in a treatment target) in a patient. Depending on the treatment modality, the degrees of freedom available for intensity modulation include beam shaping (collimation and cross-section), beam weighting (spot scanning), spot spacing (delivery pattern), spot radius (interaction range), scanning speed, beam delivery time, number of energy layers, and angle of incidence (which may be referred to as beam geometry). These degrees of freedom lead to an effectively infinite number of potential treatment plans, and therefore consistently and efficiently generating and evaluating high-quality treatment plans is beyond the capability of a human and relies on the use of a computer system, particularly considering the time constraints associated with the use of radiation therapy to treat ailments like cancer, as well as the large number of patients that are undergoing or need to undergo radiation therapy during any given time period. For IMPT, steep dose gradients are often used at the target border and field edges to enhance dose conformity.

Embodiments according to the invention contribute to improved radiation treatment planning and the treatment itself. Treatment plans that are generated considering the present disclosure are superior for sparing healthy tissue from radiation in comparison to conventional techniques by optimizing the balance between the dose rate delivered to unhealthy tissue (e.g., a tumor) in a volume in a treatment target and the dose rate delivered to surrounding healthy tissue. Consequently, treatment planning, while still a complex task, can be improved relative to conventional treatment planning.

In summary, embodiments according to this disclosure contribute to generating and implementing treatment plans that are the most effective (relative to other plans) and with the least (or most acceptable) side effects (e.g., a lower dose rate outside of the region being treated). Thus, embodiments according to the invention can improve the field of radiation treatment planning specifically and the field of radiation therapy in general.

In addition to radiation therapy techniques such as IMRT and IMPT, embodiments according to the invention can be used in spatially fractionated radiation therapy including high-dose spatially fractionated grid radiation therapy, minibeam radiation therapy, and microbeam radiation therapy.

Defining Dose Rate for Pencil Beam Scanning

Embodiments according to the present invention provide methods and systems that consider dose accumulation in a local region or sub-volume (e.g., a voxel) as a function of time. More specifically, in embodiments, methods are disclosed for (i) calculating the dose rate of voxels within a particle beam (e.g., proton beam) treatment field delivered using pencil beam scanning (PBS), also known as spot scanning, and (ii) reporting a representative dose rate for the PBS treatment field. These methods and related operations can be performed using the TPS 150 of FIG. 1.

Embodiments according to the present invention contribute to the development of improved methods that can be used for generating radiation treatment plans for radiation therapy (RT) including FLASH RT. For FLASH RT, dose rates of at least 40 Gy in less than one second, and as much as 120 Gy per second or more, may be used.

The disclosed methods take into account the unique spatiotemporal delivery patterns of PBS FLASH radiotherapy. This provides a framework for determining and describing PBS dose rate in a precise and consistent manner, a necessary requirement for cross-investigational comparison of FLASH results. Thus, these methods also can advance the research and application of PBS FLASH radiotherapy and thereby contribute to improved radiation treatment planning.

Figures 2A, 2B, 2C:
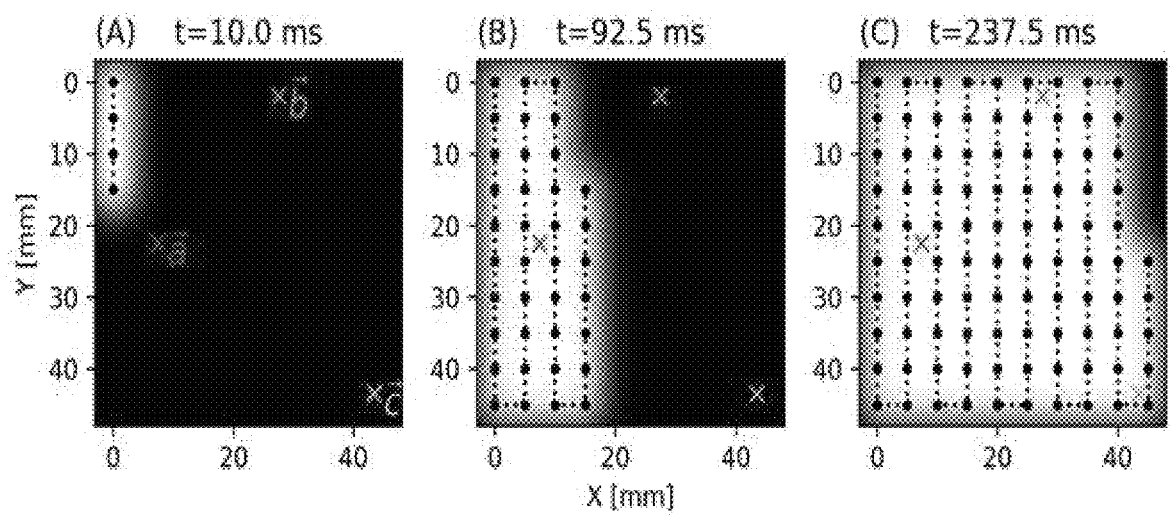
FIGS. 2A, 2B, and 2C illustrate an example of a pencil beam scanning (PBS) pattern as a function of time, in embodiments according to the present invention.

FIGS. 2A, 2B, and 2C illustrate a pencil beam scanning pattern as a function of time in embodiments according to the present invention. The example of FIGS. 2A-2C considers a mono-energetic field delivery (in other words, no energy layer switching) for simplicity of discussion and illustration. FIG. 2A shows the spots irradiated in the first 10 milliseconds (ms); FIG. 2B shows the spots irradiated after 92.5 ms; and FIG. 2C shows the spots irradiated after 237.5 ms. The scanning pattern is shown as a dotted line in FIGS. 2A-2C.

FIGS. 3A, 3B, 3C, and 3D illustrate the dose accumulation and instantaneous dose rate as a function of time for the three selected points ($\vec{a}$, $\vec{b}$, and $\vec{c}$) shown in FIGS. 2A-2C, in embodiments according to the invention.

Figure 3A:
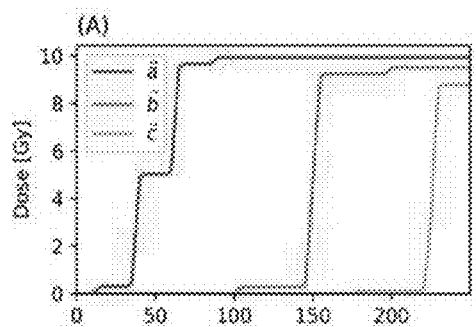
FIGS. 3A, 3B, 3C, and 3D illustrate an example of dose accumulation and instantaneous dose rate, each as a function of time, for locations identified in FIGS. 2A, 2B, 2C, in embodiments according to the invention.
Figure 3B:
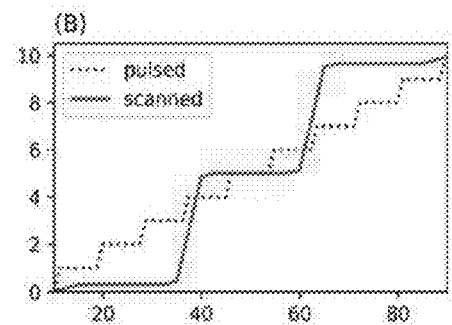
Figure 3C:
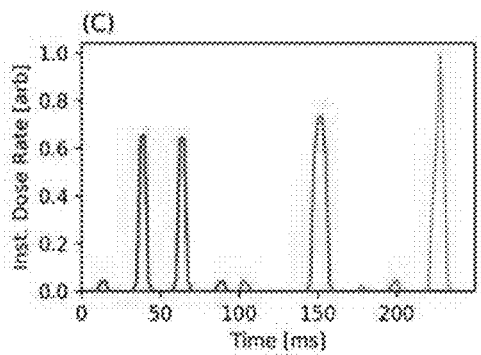

FIGS. 3A and 3C show, respectively, the cumulative dose and the instantaneous dose rate plotted for the three points ($\vec{a}$, $\vec{b}$, and $\vec{c}$) of interest identified in FIG. 2A, demonstrating that the time to accumulate the total dose at a given point is limited to a fraction of the total field delivery time.

Figure 3D:
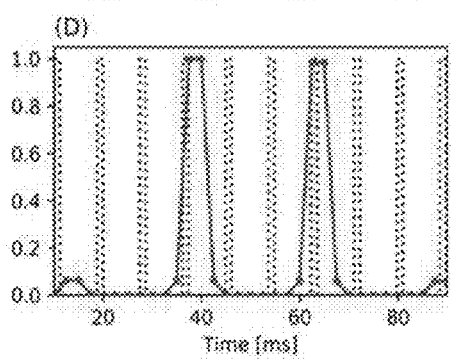

FIGS. 3B and 3D show, respectively, an example electron broad beam FLASH (bbFLASH) (dotted curve) and PBS (solid line) delivery, and also show the cumulative dose and the instantaneous dose rate, respectively, for the point $\vec{a}$ in FIG. 2A as a function of time. These figures provide a comparison of the characteristics of the time-dependent dose accumulation for the point d with that of a similar point in an electron bbFLASH field delivered in a series of pulses. FIGS. 3B and 3D show that the intra-spot dose rate for PBS is analogous to the instantaneous dose rate for bbFLASH.

The examples of FIGS. 2A-2C and 3A-3D demonstrate the value of considering the dose accumulation in a local region or sub-volume (e.g., voxel) of a PBS field as a function of time. Accounting for the dose accumulation time of individual voxels is beneficial for PBS planning and treatment and for studying FLASH RT, particularly because the FLASH effect may depend on the average dose rate.

In embodiments, generally speaking, the dose rate at each voxel of a PBS radiation field is approximated as the quotient of the voxel's dose and the voxel's "effective irradiation time." As used herein, each voxel's effective irradiation time starts when the cumulative dose at the voxel rises above a first threshold dose value, and stops when the cumulative dose at the voxel reaches a second threshold dose value. In an embodiment, the second threshold dose value is the total dose at the voxel minus the first threshold dose value. The above quotient yields a distribution of dose rates for the voxels within the PBS treatment field.

To determine and report a representative dose rate for the PBS treatment field, a measure of the dose rate distribution that is above a specified dose rate is determined. In an embodiment, a user-selectable parameter p is used to determine the $p^{th}$ percentile of the dose rate distribution, such that (100−p) percent of the treatment field is above the specified dose rate. For example, if p is five, then 95 percent of the treatment field is above a specified dose rate.

Figure 4A:
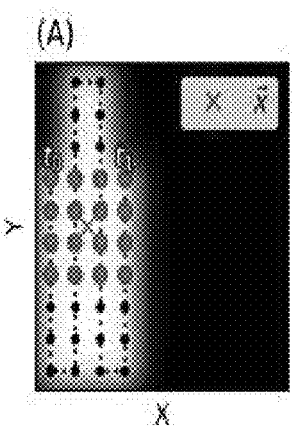
FIG. 4A illustrates an example of a PBS pattern as a function of time, in embodiments according to the present invention.
Figure 4B:
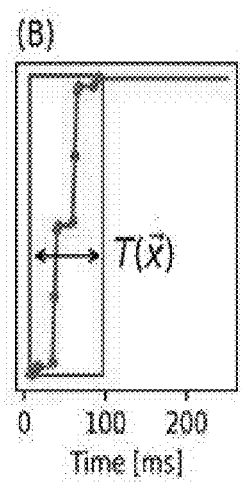
FIGS. 4B and 4C illustrate an example of dose at a location in a treatment field as a function of time, in embodiments according to the present invention.
Figure 4C:
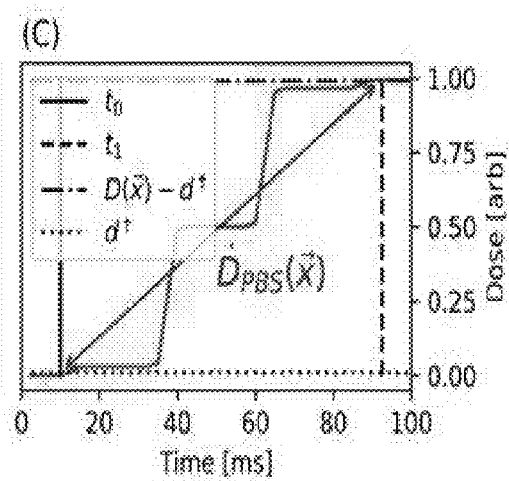

Reference is now made to FIGS. 4A, 4B, and 4C. FIG. 4A illustrates a PBS pattern as a function of time in embodiments according to the present invention. FIGS. 4B and 4C are plots of dose $d(\vec{x}, t)$ (in arbitrary units) at a location $\vec{x}$ as a function of time t in embodiments according to the present invention.

In FIG. 4A, an "X" indicates an example of the location $\vec{x}$ within the treatment field. The larger dots in FIG. 4A indicate the PBS spots that contribute significant dose to the location $\vec{x}$. The times $t_0$ and $t_1$ indicate the beginning and end of the effective irradiation time $T(\vec{x})$ the location $\vec{x}$: $T(\vec{x})=t_1-t_0$. That is, at time $t_0$ the first threshold dose value (mentioned above) is reached, and at time $t_1$ the second threshold dose value is reached.

FIG. 4B shows that most of the dose accumulation is within a relatively narrow window of time (indicated by the rectangle in the figure). In the example of FIG. 4B, most of the dose is delivered between 10.0 ms and 92.5 ms of the PBS field delivery period.

FIG. 4C expands the time axis of FIG. 4B and illustrates a graphical example of the effective irradiation time $T(\vec{x})=t_1-t_0$ and the first and second dose threshold values for the location $\vec{x}$ in the PBS field. In the example of FIG. 4C, the first threshold dose value is $d^{\dagger}$ and the second threshold dose value is $D(\vec{x})-d^{\dagger}$, where $D(\vec{x})$ is the total dose delivered to the location $\vec{x}$ within the full field application time $t_f$. The value of $d^{\dagger}$ is a user-selectable input parameter.

Continuing with reference to FIGS. 4A-4C, consider a two-dimensional (2D) plane near the surface of a PBS field as shown in FIGS. 2A-2C. The total dose D delivered to the location $\vec{x}$ within the full field application time $t_f$ can be expressed as:

$$D(\vec{x})=d(\vec{x},t_f),$$

with the corresponding average or "field" dose rate computed as:

$$\dot{D}_{field}(\vec{x}) = \frac{D(\vec{x})}{t_f}.$$

However, as shown in FIGS. 3A-3D, most of the dose accumulation at the location $\vec{x}$ occurs only during a fraction of the full field application time $t_f$. As noted above, for example, FIG. 4B illustrates that the dose accumulated at the location $\vec{x}$ (at the X in in FIG. 4A) occurs between 10.0 ms and 92.5 ms of the 250 ms PBS field delivery time period. The PBS dose rate defined as disclosed herein accounts for this situation. For that purpose, consider the effective irradiation time $T(\vec{x})=t_1-t_0$. In embodiments, the times $t_0$ and $t_1$ can be defined in terms of the dose $d(\vec{x}, t)$ by the following expressions:

$$d(\vec{x},t_0)=d^{\dagger}, \text{ and}$$

$$d(\vec{x}, t_1) = D(\vec{x}) - d^\dagger.$$

In other words, in an embodiment, the effective irradiation time $T(\vec{x})$ starts at time $t_0$ when the accumulated dose at the location $\vec{x}$ exceeds a first threshold dose value of $d^\dagger$, and ends at time $t_1$ when the accumulated dose at the location $\vec{e}$ exceeds a second threshold dose value; that is, the effective irradiation time ends when the accumulated dose at the location $\vec{x}$ is within $d^\dagger$ of the total dose $D(\vec{x})$. FIG. 4C shows a graphical example of how $T(\vec{x})$ can be computed. In the present embodiment, the PBS dose rate at the location $\vec{x}$ is the quotient of $[D(\vec{x}) - 2d^\dagger]$ and $T(\vec{x})$:

$$\dot{D}_{PBS}(\vec{x}) = \frac{D(\vec{x}) - 2d^\dagger}{T(\vec{x})}.$$

Figures 5A, 5B, 5C:
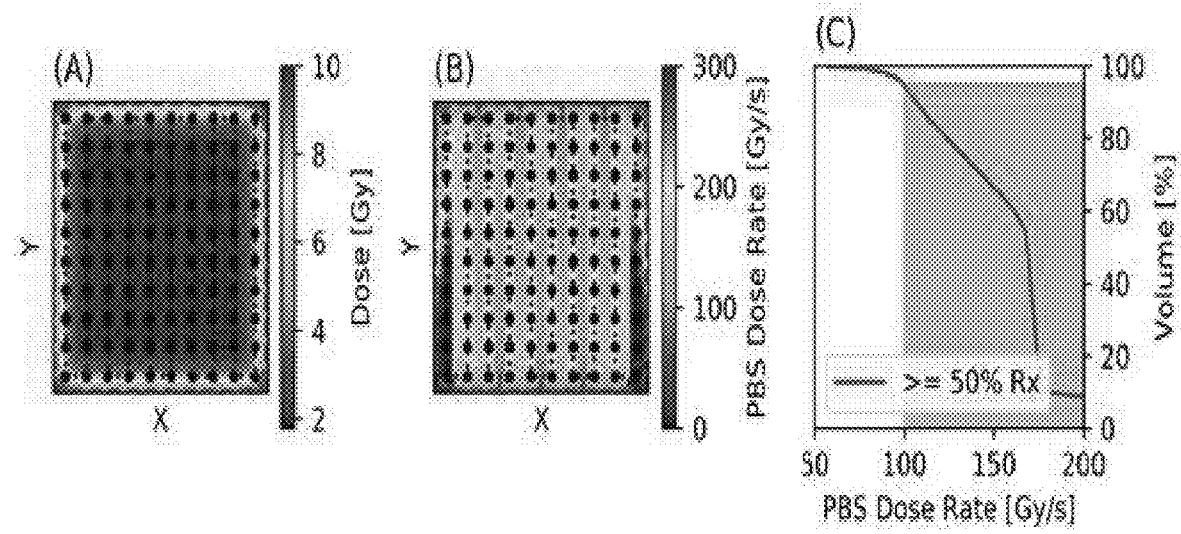
FIG. 5A illustrates an example of a dose distribution, in embodiments according to the invention.
FIG. 5B illustrates an example of a PBS dose rate distribution, in embodiments according to the invention.
FIG. 5C illustrates an example of a dose rate-volume histogram, in embodiments according to the invention.

FIG. 5A is a plot of the dose distribution, and FIG. 5B is a plot of the PBS dose rate distribution, for a matrix of 113×113 points just below the surface of a five-by-five centimeter (cm) monoenergetic (250 MeV) PBS treatment field in an example in embodiments according to the invention. The 50 percent isodose line is plotted with a dashed line at the peripheries of the fields shown in FIGS. 5A and 5B. The scanning pattern and spot locations are plotted with dotted line and circles, respectively. In this example, the prescription dose is 10 Gy.

FIG. 5C shows the dose rate-volume histogram (DRVH) for the area enclosed by the 50 percent isodose line in FIG. 5B (where dose is greater than or equal to 50 percent of the prescription dose). As indicated by the rectangle in FIG. 5C, 95 percent of the points have an effective dose rate exceeding 100 Gy/sec.

In the example of FIGS. 5A-5C, the dose and dose rate distributions for the examples shown in the previous figures above are calculated with a dose grid spacing of 0.5 millimeters (mm) in all dimensions and are shown as color-wash displays in FIGS. 5A and 5B. The uniform dose distribution in FIG. 5A is by design.

The first notable observation is the dissimilarity of the dose and PBS dose rate distributions. In the PBS dose rate distribution (FIG. 5B), two salient features are apparent: a discrete and a continuous variation of the dose rate.

The discrete behavior can be understood as follows. Practically, the effective irradiation time $T(\vec{x})$ reflects the time required to traverse the scanning path between the spots delivered at times $t_0$ and $t_1$, as illustrated in FIG. 4A. In FIG. 4A, the point of interest $\vec{x}$ requires inclusion of just over three lines of spots. However, considering voxels along the x-axis in FIG. 5B, the total number of scan lines could vary between two and four depending on the relative position of a voxel to a scan line, the spot spacing, and the spot radius (interaction range). As a result, the effective irradiation time $T(\vec{x})$ would increase or decrease significantly, thereby drastically changing the dose rate. The discrete nature of both the delivery pattern and spot interaction range (imposed by the selected value of the threshold $d^\dagger$) result in dose rate discontinuities in this situation.

Referring to the DRVH in FIG. 5C, to understand the continuous variation of the PBS dose rate across the field (gradients along the y-axis in FIG. 5B), consider the delivery path lengths required to deliver contributing spots as a function of the y-position in the field. Generally speaking, the number of scan lines that influence the effective irradiation time $T(\vec{x})$ will decrease as the location of the point of interest $\vec{x}$ approaches an edge where the spot pattern is not connected (an edge opposite a u-turn in the pattern), with the extreme minimum being at the corners of the treatment field opposite the beginning and end of the pattern. With reference to FIG. 5B, this is exemplified by the dose rate for a central voxel that is lower than that for a voxel at the edge, with maxima at the two lower corners of the treatment field (here, the terms "upper" and "lower" refer to the orientation of the treatment field in the figures). The reason for the dose rate being high in only two corners has to do with the nature of the scanning pattern. Specifically, those points in the upper corners of the treatment field include scan time contributions from many more spots than the points in the lower corners, which have only a few neighboring lines contributing to the effective irradiation time $T(\vec{x})$.

To illustrate the fundamental characteristics of the PBS dose rate in 3D, the dose rate $\dot{D}_{PBS}(\vec{x})$ distribution is calculated for a 250 MeV monoenergetic 10×10 $cm^2$ proton field delivering 10 Gy to at the isocenter located at a depth of 10 cm in a water phantom with an in-air spot sigma of approximately 3.3 mm. For simplicity, but without loss of generality, a quasi-static spot delivery is assumed, in which the dose is deposited to points on a five mm square grid assuming two ms spot delivery time with a scanning speed of 10 mm per second. These parameters are nominally representative of modern scanning systems. Based on these values, the total dose delivery plus beam traversal time is 2.5 ms per spot, for a total field delivery time of 1000 ms, and a dose rate $\dot{D}_{field}$ of 10 Gy per second.

For a prescribed dose of 10 Gy, a reasonable threshold value of 0.1 Gy is chosen for $d^\dagger$. The dose rate $\dot{D}_{PBS}(\vec{x})$ distribution was calculated with a grid spacing of 2.5 mm in all dimensions.

Figures 6A, 6B:
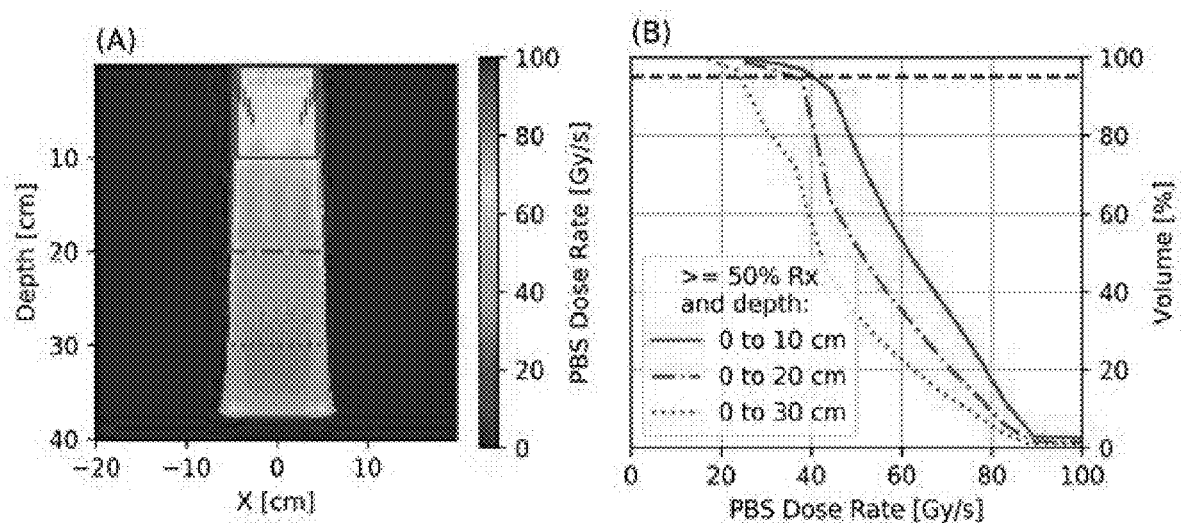
FIG. 6A illustrates an axial view of an example of a three-dimensional PBS dose rate distribution, in embodiments according to the invention.
FIG. 6B illustrates an example of a histogram of PBS dose rate versus volume for regions at different depths of a treatment field, in embodiments according to the invention.
Figure 6C:
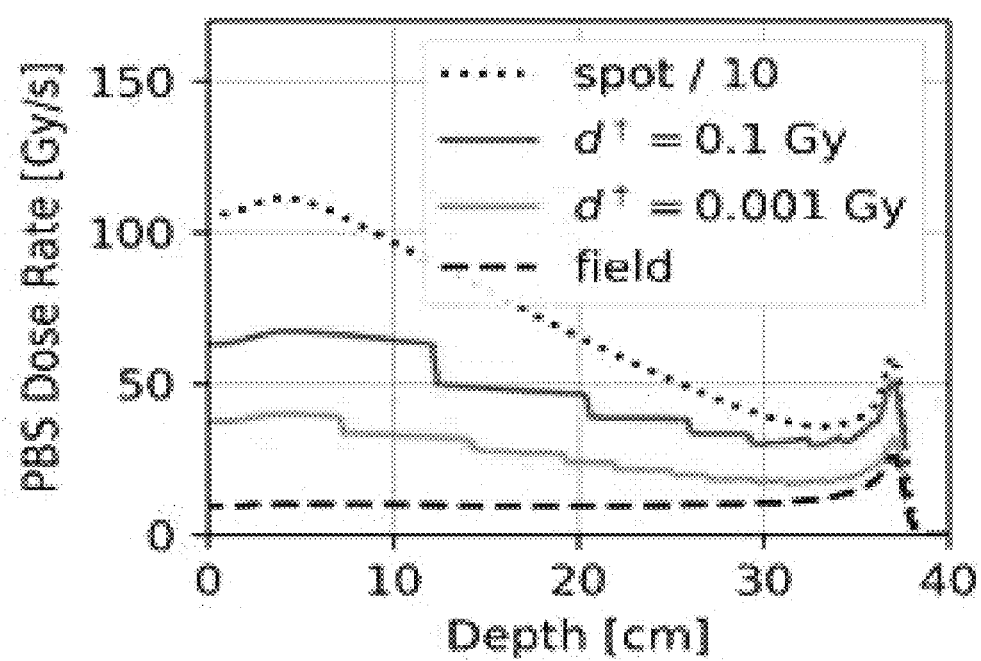
FIG. 6C illustrates an example of PBS dose rate versus depth at the center of the treatment field, in embodiments according to the invention.

Results of the above calculation are shown in FIGS. 6A, 6B, and 6C. FIG. 6A is a color-wash display of the axial view of a three-dimensional (3D) PBS dose rate distribution for the example, in embodiments according to the invention. FIG. 6B illustrates a histogram of PBS dose rate versus volume for regions at different depths of the treatment target that receive at least 50 percent of the prescription dose for the example, in embodiments according to the invention. FIG. 6C illustrates PBS dose rate versus depth at the center of the treatment field for the example, in embodiments according to the invention.

An apparent feature is the decrease in dose rate with depth, which is displayed quantitatively in FIG. 6C. The dose rate decreases in the irradiated volume with increasing depth (until the Bragg peak) due to the increase in pencil beam radius (and the radius of influence) with depth due to multiple coulomb-scattering. As a result, the spot size relative to the scanning pattern dimension grows, leading to an increase of the effective irradiation time $T(\vec{x})$ with depth and hence a corresponding decrease in dose rate. The DRVH of FIG. 6B quantifies the decrease in dose rate with increasing depth. Specifically, in this example, 95 percent of the irradiated volume (defined as the region receiving at least 50 percent of the prescription dose) at depths between zero and 10 cm depth receive more than 40 Gy per second, whereas at depths from 0-20 cm and from 0-30 cm depth, 95 percent of the irradiated volume receive more than 36 Gy per second and more than 24 Gy per second, respectively.

The decrease in dose rate with depth can be modulated by the choice of the threshold $d^\dagger$. FIG. 6C shows representative depth dose rate (DDR) curves for two values of $d^\dagger$ (0.1 Gy and 0.001 Gy). The results show that the dose rate decreases as the threshold $d^\dagger$ is decreased, and approaches the field dose rate when the threshold $d^\dagger$ nears zero. The PBS DDR trends toward that of a single spot with increasing values of the threshold $d^\dagger$, and toward that of a uniform field with decreasing values of the threshold $d^\dagger$. The origin for this is analogous to the 2D discrete features. The abrupt changes in dose rate for the middle two curves are due to quick increases in the effective irradiation time $T(\vec{x})$ when the spot size is increased to include more spots that contribute to the dose at the location $\vec{x}$.

To summarize to this point, disclosed herein is a novel method to calculate the dose rate at each voxel of a scanned pencil beam, taking into account the relationship of dose accumulation and irradiation time at that voxel. The method can be applied in 2D and in 3D. While the discussion above is for an example of discrete spot delivery, it can be applied to continuous scanning so long as the dose $d(\vec{x}, t)$ is known, with the beam flux and scanning speed as input parameters. In addition, the example can be extended to PBS delivery using an extended Bragg peak or any other PBS-like dose delivery.

As described above, there is a user selectable parameter: the threshold value for accumulated dose $d^\dagger$ that, when reached, starts the clock for measuring the effective irradiation time for a voxel. In embodiments, the same threshold value applies in ending the irradiation time, when the delivered dose comes within the total dose at the voxel minus the threshold value $d^\dagger$. In one of the above examples, a value of 0.1 Gy, or one percent of the prescribed dose of 10 Gy, is selected as the threshold. Selection of a different threshold value will affect the value of effective irradiation time and thereby affect the calculated value of dose rate. Specifically, a decrease in the threshold value will lead to an increase in effective irradiation time (relative to that of the total field in the limit as the threshold value $d^\dagger$ approaches zero) and a decrease in calculated dose rate.

As there is a distribution in the calculated dose rate $\dot{D}_{PBS}(\vec{x})$ (e.g., see FIG. 5B) for a PBS field, it is necessary to meaningfully and succinctly characterize a representative PBS dose rate. Such choices include the average, mean, median, and minimum dose rates in the calculated dose rate distribution. For FLASH RT, because the biological effect seems to be present only above a certain dose rate, selecting the minimum dose rate might seem logical. However, that choice may be skewed by outliers. Therefore, in embodiments according to the invention, another user-selectable parameter p is used, corresponding to the $p^{th}$ percentile of the $\dot{D}_{PBS}(\vec{x})$ dose rate distribution, such that (100−p) percent of the treatment field is above the corresponding dose rate. In the example of FIG. 5C, the 5th percentile is selected, such that 95 percent of the treatment field is above the dose rate of 100 Gy per second.

The selection of values for threshold $d^\dagger$ and the percentile p influences the reported PBS dose rate. To the extent that the FLASH phenomenon is dependent on dose rate, there may be implications in correlating the reported PBS dose rate with radiobiological observations. For instance, selecting the $5^{th}$ percentile as the representative dose rate means that there is five percent of the treatment volume receiving less than the desired FLASH dose rate. Thus, it can be of importance for further study and understanding of FLASH to standardize the nomenclature for reporting the representative or effective dose rate of a PBS treatment field (e.g., a proton field). For a given region of interest (e.g., the 50 percent isodose line), nomenclature of the form $\dot{D}_{d^\dagger,p}$ is used to denote that the dose rate is for a threshold $d^\dagger$ and a percentile p in the dose rate distribution selected for the effective dose rate. For the example of FIG. 6B, the reported effective dose rate is $\dot{D}_{0.1,5}$=40 Gy per second for the irradiated volume between zero and 10 cm depth, meaning that 95 percent of that volume has at least a dose rate of 40 Gy per second when the threshold value ($d^\dagger$) is 0.1 Gy.

Figure 7:
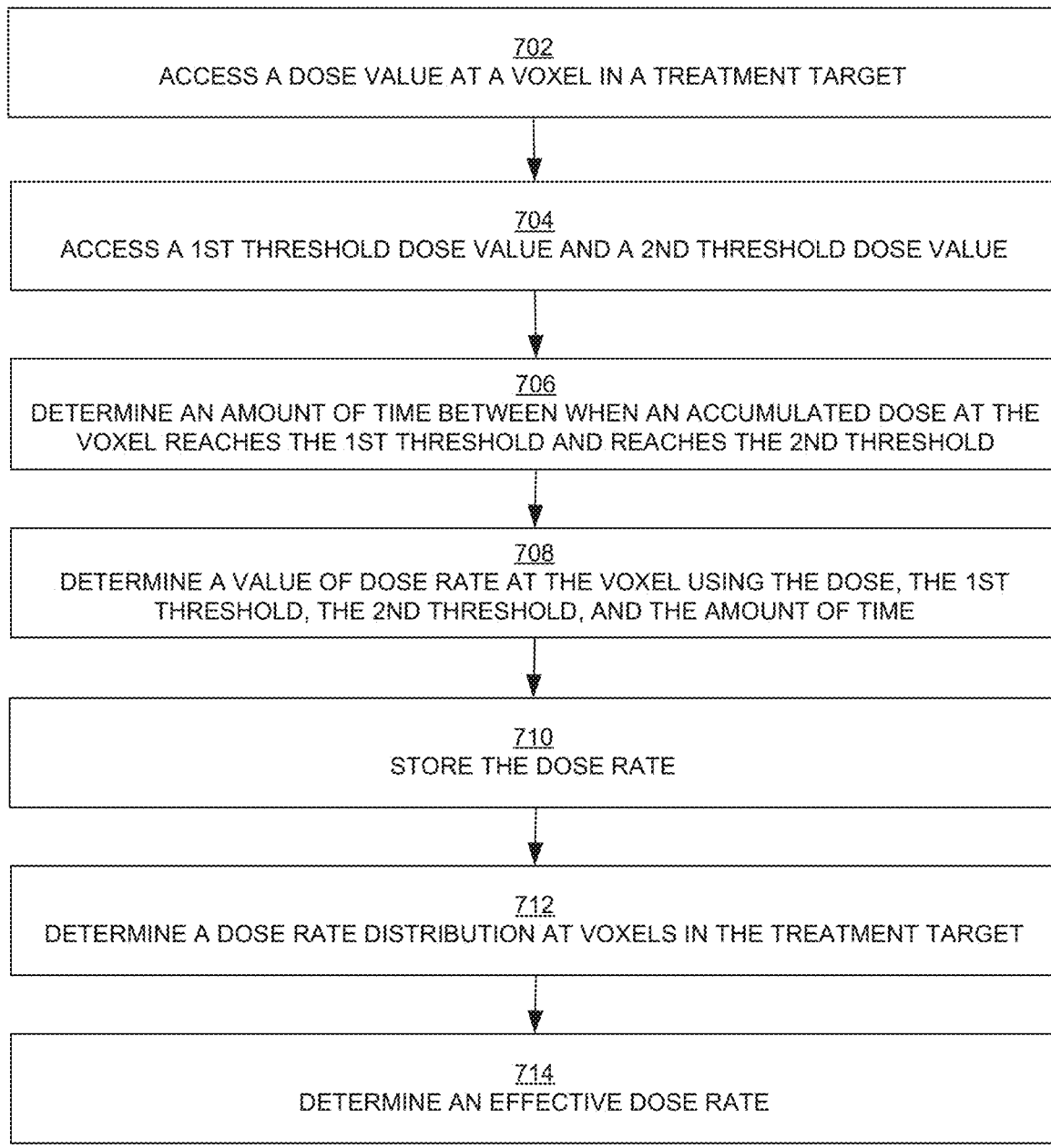
FIG. 7 is a flowchart of an example of a computer-implemented method that can be used in radiation treatment planning in embodiments according to the present invention.

FIG. 7 is a flowchart 700 of examples of a computer-implemented method in embodiments according to the present invention. The flowchart 700 can be implemented as computer-executable instructions (e.g., the TPS 150 of FIG. 1) residing on some form of computer-readable storage medium (e.g., in system memory 104 of the computer system 100 of FIG. 1).

While the operations in the flowchart of FIG. 7 are presented as occurring in series and in a certain order, the present invention is not so limited. The operations may be performed in a different order and/or in parallel, and they may also be performed in an iterative manner. As noted above, because of the different parameters that need to be considered, the range of values for those parameters, the interrelationship of those parameters, the need for treatment plans to be effective yet minimize risk to the patient, the need to generate high-quality treatment plans quickly, and the need for studying the FLASH effect consistently, the use of the TPS 150 executing reliably on the computer system 100 (FIG. 1) as disclosed herein is important for radiation treatment planning as well as for studying and understanding the FLASH effect.

In block 702 of FIG. 7, a dose value at a voxel in a treatment target is accessed.

In block 704, a first threshold dose value and a second threshold dose value are accessed or determined. In an embodiment, the second threshold dose value is the difference between a total dose value for the voxel and the first threshold dose value.

In block 706, an amount of time between a time when an accumulated dose at the voxel reaches the first dose value threshold and a time when the accumulated dose at the voxel reaches the second threshold dose value is determined or measured.

In block 708, a value of dose rate at the voxel is determined using the dose value at the voxel, the first threshold dose value, the second threshold dose value, and the amount of time.

In block 710, the value of dose rate (from block 708) is stored in system memory 104 as a candidate parameter in a radiation treatment plan.

In block 712, a dose rate distribution at voxels in the treatment target is determined. A selected value (e.g., isoline) of the dose rate is accessed. A measure (e.g., percentile) of the dose rate distribution that exceeds the selected value is determined. The dose rate distribution can be determined as a function of depth in the treatment target.

In block 714, an effective dose rate value that is representative of the dose rate distribution is determined and stored in system memory 104. The value of the measure and the first threshold dose value (blocks 712 and 704, respectively) are associated with the effective dose rate value in the computer system memory.

In summary, embodiments according to the present invention consider the scanning time for PBS (spot scanning) in general and PBS FLASH radiotherapy in particular. By considering the scanning time, the temporal separation between dose deliveries to the spots is accounted for, and as a result the dose rate estimate for an array of spots accounts for the time period required to accumulate the dose.

Embodiments according to the present invention provide methods and systems that consider dose accumulation in a local region or sub-volume (e.g., a voxel) as a function of time. More specifically, in embodiments, methods are disclosed for (i) calculating the dose rate of voxels within a particle beam (e.g., proton beam) treatment field delivered using PBS (in other words, the dose rate distribution of a PBS treatment field), and (ii) reporting a representative dose rate for the PBS treatment field.

The disclosed methods take into account the unique spatiotemporal delivery patterns of PBS FLASH radiotherapy. This provides a framework for determining and describing PBS dose rate in a precise and consistent manner, a necessary requirement for cross-investigational comparison of FLASH results. These methods can be used for radiation treatment planning as well as for advancing the research and application of PBS FLASH radiotherapy.

In summary, embodiments according to the invention contribute to improved radiation treatment planning and the treatment itself. Treatment plans generated as described herein are superior for sparing normal tissue from radiation in comparison to conventional techniques by reducing, if not minimizing, the magnitude (and the integral in some cases) of the dose to normal tissue (outside the target) by design. When used with FLASH dose rates, management of patient motion is simplified because the doses are applied in a short period of time (e.g., less than a second).

In addition to radiation therapy techniques in which the intensity of the particle beam is either constant or modulated across the field of delivery, such as IMRT and IMPT, embodiments according to the invention can be used in spatially fractionated radiation therapy including high-dose spatially fractionated grid radiation therapy, minibeam radiation therapy, and microbeam radiation therapy. The techniques described herein may be useful for stereotactic radiosurgery as well as stereotactic body radiotherapy with single or multiple metastases.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A computer system, comprising:
a processor; and
a memory coupled to the processor and comprising instructions that, when executed, cause the processor to perform a method used for planning a radiation treatment, the method comprising:
accessing information comprising a dose value at a voxel in a treatment target;
accessing information comprising a first threshold dose value and a second threshold dose value greater than the first threshold dose value;
determining an amount of time between a time when an accumulated dose at the voxel reaches the first threshold dose value and a time when the accumulated dose at the voxel reaches the second threshold dose value;
determining a dose rate value at the voxel using the dose value at the voxel in the treatment target, the first threshold dose value, the second threshold dose value, and the amount of time; and
storing the dose rate value as a candidate parameter in a radiation treatment plan.

2. The computer system of claim 1, wherein the second threshold dose value comprises a difference between a total dose value for the voxel and the first threshold dose value.

3. The computer system of claim 1, wherein the method further comprises:
determining a dose rate distribution comprising dose rate values at a plurality of voxels in the treatment target;
accessing information comprising a selected dose rate value; and
determining a measure of the dose rate distribution that exceeds the selected dose rate value.

4. The computer system of claim 3, wherein the method further comprises storing, in the memory, an effective dose rate value that is representative of the dose rate distribution.

5. The computer system of claim 4, wherein storing the effective dose rate value further comprises associating, in the memory, the effective dose rate value with the measure of the dose rate distribution that exceeds the selected dose rate value, and the first threshold dose value.

6. The computer system of claim 3, wherein the dose rate distribution is a function of a depth in the treatment target.

7. The computer system of claim 3, wherein the dose rate distribution is determined using values of parameters selected from the group consisting of: a beam energy; a beam delivery pattern; an interaction range; a beam cross-sectional area; a beam scanning speed; and a beam delivery time.

8. A non-transitory computer-readable storage medium having computer-executable instructions for causing a computer system to perform a method used for planning a radiation treatment, the method comprising:
accessing information comprising a dose value at a voxel in a treatment target;
accessing information comprising a first threshold dose value and a second threshold dose value greater than the first threshold dose value;
determining an amount of time between a time when an accumulated dose at the voxel reaches the first threshold dose value and a time when the accumulated dose at the voxel reaches the second threshold dose value;
determining a dose rate value at the voxel using the dose value at the voxel in the treatment target, the first threshold dose value, the second threshold dose value, and the amount of time; and
storing the dose rate value as a candidate parameter in a radiation treatment plan.

9. The non-transitory computer-readable storage medium of claim 8, wherein the second threshold dose value comprises a difference between a total dose value for the voxel and the first threshold dose value.

10. The non-transitory computer-readable storage medium of claim 8, wherein the method further comprises:
determining a dose rate distribution comprising dose rate values at a plurality of voxels in the treatment target;
accessing information comprising a selected dose rate value; and
determining a measure of the dose rate distribution that exceeds the selected dose rate value.

11. The non-transitory computer-readable storage medium of claim 10, wherein the method further comprises storing, in the memory, an effective dose rate value that is representative of the dose rate distribution.

12. The non-transitory computer-readable storage medium of claim 11, wherein storing the effective dose rate value further comprises associating, in the memory, the effective dose rate value with the measure of the dose rate distribution that exceeds the selected dose rate value, and the first threshold dose value.

13. The non-transitory computer-readable storage medium of claim 10, wherein the dose rate distribution is a function of a depth in the treatment target.

14. The non-transitory computer-readable storage medium of claim 10, wherein the dose rate distribution is determined using values of parameters selected from the group consisting of: a beam energy; a beam delivery pattern; an interaction range; a beam cross-sectional area; a beam scanning speed; and a beam delivery time.

15. A computer-implemented method used for radiation treatment planning, the computer-implemented method comprising:
    accessing information comprising a dose value at a voxel in a treatment target;
    accessing information comprising a first threshold dose value and a second threshold dose value greater than the first threshold dose value;
    determining an amount of time between a time when an accumulated dose at the voxel reaches the first threshold dose value and a time when the accumulated dose at the voxel reaches the second threshold dose value;
    determining a dose rate value at the voxel using the dose value at the voxel in the treatment target, the first threshold dose value, the second threshold dose value, and the amount of time; and
    storing the dose rate value as a candidate parameter in a radiation treatment plan.

16. The computer-implemented method of claim 15, wherein the second threshold dose value comprises a difference between a total dose value for the voxel and the first threshold dose value.

17. The computer-implemented method of claim 15, further comprising:
    determining a dose rate distribution comprising dose rate values at a plurality of voxels in the treatment target;
    accessing information comprising a selected dose rate value; and
    determining a measure of the dose rate distribution that exceeds the selected dose rate value.

18. The computer-implemented method of claim 17, further comprising storing an effective dose rate value that is representative of the dose rate distribution.

19. The computer-implemented method of claim 18, wherein storing the effective dose rate value further comprises associating, in the memory, the effective dose rate value with the measure of the dose rate distribution that exceeds the selected dose rate value, and the first threshold dose value.

20. The computer-implemented method of claim 17, wherein the dose rate distribution is a function of a depth in the treatment target.

21. The computer-implemented method of claim 17, wherein the dose rate distribution is determined using values of parameters selected from the group consisting of: a beam energy; a beam delivery pattern; an interaction range; a beam cross-sectional area; a beam scanning speed; and a beam delivery time.

* * * * *